United States Patent
Zhang

(10) Patent No.: US 9,694,011 B2
(45) Date of Patent: Jul. 4, 2017

(54) SUBSTITUTED PYRAZOLOPYRIMIDINES AS KINASES INHIBITORS

(71) Applicant: JIANGSU MEDOLUTION LTD, Taizhou (CN)

(72) Inventor: Dawei Zhang, Thousand Oaks, CA (US)

(73) Assignee: Jiangsu Medolution Ltd, Taizhou (CN)

( * ) Notice: Subject to any disclaimer, the term of this patent is extended or adjusted under 35 U.S.C. 154(b) by 0 days.

(21) Appl. No.: 14/893,044

(22) PCT Filed: May 21, 2014

(86) PCT No.: PCT/CN2014/078007
§ 371 (c)(1),
(2) Date: Nov. 20, 2015

(87) PCT Pub. No.: WO2014/187319
PCT Pub. Date: Nov. 27, 2014

(65) Prior Publication Data
US 2016/0120868 A1 May 5, 2016

Related U.S. Application Data

(60) Provisional application No. 61/855,669, filed on May 21, 2013.

(51) Int. Cl.
*A61K 31/519* (2006.01)
*C07D 487/04* (2006.01)
*A61K 45/06* (2006.01)

(52) U.S. Cl.
CPC ............ *A61K 31/519* (2013.01); *A61K 45/06* (2013.01); *C07D 487/04* (2013.01)

(58) Field of Classification Search
CPC .................................................. C07D 487/04
See application file for complete search history.

(56) References Cited

U.S. PATENT DOCUMENTS

| 8,673,925 B1 | 3/2014 | Goldstein |
| 2008/0076921 A1 | 3/2008 | Honigberg et al. |

FOREIGN PATENT DOCUMENTS

| WO | 2008121742 A2 | 10/2008 |
| WO | 2010009342 A2 | 1/2010 |
| WO | 2013003629 A2 | 1/2013 |

*Primary Examiner* — Brian McDowell
(74) *Attorney, Agent, or Firm* — Feng Tian

(57) ABSTRACT

The present invention is directed to novel pyrazolopyrimidines such as compounds of Formula I, their derivatives, pharmaceutically acceptable salts, solvates and hydrates thereof. The compounds and compositions of the present invention have protein kinases inhibitory activities against BTK and/or EGFR T790M and are useful for the treatment of protein kinases mediated diseases and conditions.

3 Claims, No Drawings

SUBSTITUTED PYRAZOLOPYRIMIDINES AS KINASES INHIBITORS

CROSS REFERENCE TO RELATED APPLICATION

This invention claims the benefit of U.S. Provisional Patent Application No. 61/855,669 filed on May 21, 2013, which is incorporated herein by reference in its entirety.

FIELD OF THE INVENTION

The present invention is directed to inhibitors of kinase and pharmaceutically acceptable salts, solvates, hydrates, prodrugs and metabolites thereof, the preparation method thereof, and the use of such compounds to treat kinase mediated diseases and conditions such as cancer.

BACKGROUND OF THE INVENTION

Protein kinases represent a large family of enzymes, which catalyze the phosphorylation of target protein substrates. The phosphorylation is usually a transfer reaction of a phosphate group from ATP to the protein substrate. Common points of attachment for the phosphate group to the protein substrate include, for example, a tyrosine, serine or threonine residue. Due to their activity in numerous cellular processes, protein kinases have emerged as important therapeutic targets.

Epidermal growth factor (EGF) is a widely distributed growth factor that in cancer, can stimulate cancer-cell proliferation, block apoptosis, activate invasion and metastasis, and stimulate angiogenesis (Citri, et al., *Nat. Rev. Mol. Cell. Biol.* 7:505, 2006; Hynes, et al., *Nat. Rev. Cancer* 5:341, 2005). The EGF receptor (EGFR or ErbB) is a transmembrane, tyrosine kinase receptor that belongs to a family of four related receptors. The majority of human epithelial cancers are marked by functional activation of growth factors and receptors of this family (Ciardiello, et al., *New Eng. J. Med.* 358: 1160, 2008) so that EGF and EGFR are natural targets for cancer therapy. The human epidermal growth factor receptor (HER) tyrosine kinase family consists of four structurally related cellular receptors: the epidermal growth factor receptor (EGFR;HER1), HER2 (ErbB2), HER3 (ErbB3), and HER4. Quinazolines are a known class of kinase inhibitors with utility for the treatment of cancer, angiogenesis disorders, and inflammatory disorders. To this end, attempts have been made to identify small molecules which act as protein kinase inhibitors. For example, quinazoline derivatives (PCT WO 00177104; US20050250761; WO2004069791) have been described as HER kinase inhibitors.

EGFR inhibitors erlotinib and gefitinib as well as the dual EGFR/HER2 inhibitor lapatinib are FDA-approved cancer drugs that are effective against multiple solid tumor cancers. However, their effectiveness is also limited by the drug resistance that frequent emerges following treatment point mutations in the kinase domain of EGFR as well as upregulation of by-pass signaling pathways are frequently observed resistance mechanisms in patients treated with gefitinib and erlotinib. A single point mutation at the gatekeeper position, T790M in EGFR kinase domain accounts for approximately 50% of acquired resistance.

Thus, the compounds that can inhibit mutant protein kinases such as EGFR T790M activity with improved efficacy or overcoming drug resistance are highly desired.

Bruton's tyrosine kinase (Btk) plays a key role in promoting B cell proliferation and survival through participation in the B cell receptor (BCR) signaling pathway and represents a promising new drug target. Targeted therapies that suppress BCR signaling have emerged as promising agents in the treatment of several B cell malignancies. To this end, attempts have been made to identify small molecules which act as Btk inhibitors. For example, U.S. Pat. No. 7,982,036 describes 4,6-disubstituted pyrimidine compounds as useful kinase inhibitors targeting the Tec kinase family. The disclosed compounds include Btk inhibitors. Another class of Btk inhibitors has been disclosed in U.S. Pat. No. 8,088,781.

Thus, the compounds that can inhibit protein kinases such as Bruton's tyrosine kinase (Btk) activity are highly desired.

SUMMARY OF THE INVENTION

In some embodiments of the present invention, there are provided compounds of Formula I:

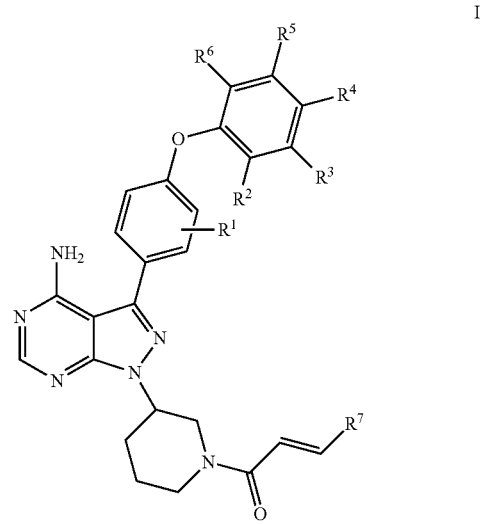

or a pharmaceutically acceptable salt, solvate or a prodrug or a stereoisomer or a tautomer or a metabolite thereof, wherein $R^1$, $R^2$, $R^3$, $R^4$, $R^5$, and $R^6$ are independently hydrogen, $C_1$-$C_6$ alkyl, $C_1$-$C_6$ alkoxy, F, Cl, CN, or $CF_3$;

$R^7$ is hydrogen, $CH_2NR^8R^9$, or $CH_2$—N-piperidine;

$R^8$ and $R^9$ are independently hydrogen or $C_1$-$C_6$ alkyl;

with the proviso that when $R^7$ is hydrogen or —$CH_2NR^8R^9$, at least one of $R^1$, $R^2$, $R^3$, $R^4$, $R^5$, and $R^6$ is not hydrogen.

The present invention further provides pharmaceutical compositions comprising a compound of Formula I described above and a pharmaceutically acceptable carrier The present invention further provides methods for regulating the kinase signaling transduction comprising administrating to a mammalian subject a therapeutically effective amount of any of the compounds of Formula I described above.

DETAILED DESCRIPTION OF THE INVENTION

In some embodiments of the present invention, there are provided compounds of Formula I:

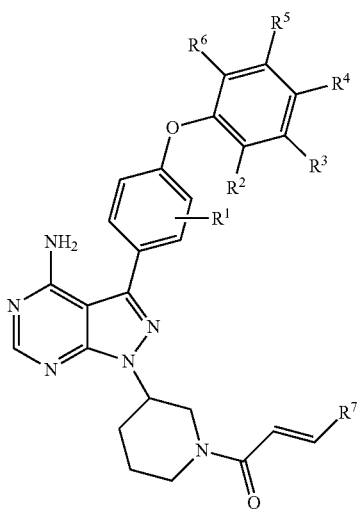

I or a pharmaceutically acceptable salt, solvate or a prodrug or a stereoisomer or a tautomer or a metabolite thereof, wherein
$R^1$, $R^2$, $R^3$, $R^4$, $R^5$, and $R^6$ are independently hydrogen, $C_1$-$C_6$ alkyl, $C_1$-$C_6$ alkoxy, F, Cl, CN, or $CF_3$;
$R^7$ is hydrogen, $CH_2NR^8R^9$, or —$CH_2$—N-piperidne;
$R^8$ and $R^9$ are independently hydrogen or $C_1$-$C_6$ alkyl;
with the proviso that when $R^7$ is hydrogen or —$CH_2NR^8R^9$, at least one of $R^1$, $R^2$, $R^3$, $R^4$, $R^5$, and $R^6$ is not hydrogen.

In some embodiments, $R^1$ and $R^4$ are independently hydrogen, F or Cl.

In other embodiments, $R^1$ is F or Cl.
In some embodiments, $R^3$ or $R^4$ is F or Cl.
In another embodiments, $R^2$ is F or Cl.
In other embodiments, $R^3$ is $CF_3$.
In some embodiments, $R^2$, $R^3$, $R^5$, $R^6$, and $R^7$ are independently hydrogen; $R^1$ and $R^4$ are independently hydrogen, F or Cl; and $R^1$ and $R^4$ are not hydrogen at the same time.

In certain embodiments, there are provided compounds without limitation selected from the group consisting of:
1-(3-(4-amino-3-(3-fluoro-4-phenoxyphenyl)-1H-pyrazolo[3,4-d]pyrimidin-1-yl)piperidin-1-yl)prop-2-en-1-one;
(R)-1-(3-(4-amino-3-(3-fluoro-4-phenoxyphenyl)-1H-pyrazolo[3,4-d]pyrimidin-1-yl)piperidin-1-yl)prop-2-en-1-one;
(S)-1-(3-(4-amino-3-(3-fluoro-4-phenoxyphenyl)-1H-pyrazolo[3,4-d]pyrimidin-1-yl)piperidin-1-yl)prop-2-en-1-one;
1-(3-(4-amino-3-(3-chloro-4-phenoxyphenyl)-1H-pyrazolo[3,4-d]pyrimidin-1-yl)piperidin-1-yl)prop-2-en-1-one;
(R)-1-(3-(4-amino-3-(3-chloro-4-phenoxyphenyl)-1H-pyrazolo[3,4-d]pyrimidin-1-yl)piperidin-1-yl)prop-2-en-1-one;
(S)-1-(3-(4-amino-3-(3-chloro-4-phenoxyphenyl)-1H-pyrazolo[3,4-d]pyrimidin-1-yl)piperidin-1-yl)prop-2-en-1-one;
1-(3-(4-amino-3-(4-(4-chlorophenoxy)phenyl)-1H-pyrazolo[3,4-d]pyrimidin-1-yl)piperidin-1-yl)prop-2-en-1-one;
(R)-1-(3-(4-amino-3-(4-(4-chlorophenoxy)phenyl)-1H-pyrazolo[3,4-d]pyrimidin-1-yl)piperidin-1-yl)prop-2-en-1-one;
(S)-1-(3-(4-amino-3-(4-(4-chlorophenoxy)phenyl)-1H-pyrazolo[3,4-d]pyrimidin-1-yl)piperidin-1-yl)prop-2-en-1-one;
1-(3-(4-amino-3-(4-(4-fluorophenoxy)phenyl)-1H-pyrazolo[3,4-d]pyrimidin-1-yl)piperidin-1-yl)prop-2-en-1-one;
(R)-1-(3-(4-amino-3-(4-(4-fluorophenoxy)phenyl)-1H-pyrazolo[3,4-d]pyrimidin-1-yl)piperidin-1-yl)prop-2-en-1-one;
(S)-1-(3-(4-amino-3-(4-(4-fluorophenoxy)phenyl)-1H-pyrazolo[3,4-d]pyrimidin-1-yl)piperidin-1-yl)prop-2-en-1-one;
1-(3-(4-amino-3-(4-(3,4-dichlorophenoxy)phenyl)-1H-pyrazolo[3,4-d]pyrimidin-1-yl)piperidin-1-yl)prop-2-en-1-one;
(R)-1-(3-(4-amino-3-(4-(3,4-dichlorophenoxy)phenyl)-1H-pyrazolo[3,4-d]pyrimidin-1-yl)piperidin-1-yl)prop-2-en-1-one;
(S)-1-(3-(4-amino-3-(4-(3,4-dichlorophenoxy)phenyl)-1H-pyrazolo[3,4-d]pyrimidin-1-yl)piperidin-1-yl)prop-2-en-1-one;
1-(3-(4-amino-3-(4-(2-chloro-4-(trifluoromethyl)phenoxy)phenyl)-1H-pyrazolo[3,4-d]pyrimidin-1-yl)piperidin-1-yl)prop-2-en-1-one;
(R)-1-(3-(4-amino-3-(4-(2-chloro-4-(trifluoromethyl)phenoxy)phenyl)-1H-pyrazolo[3,4-d]pyrimidin-1-yl)piperidin-1-yl)prop-2-en-1-one;
(S)-1-(3-(4-amino-3-(4-(2-chloro-4-(trifluoromethyl)phenoxy)phenyl)-1H-pyrazolo[3,4-d]pyrimidin-1-yl)piperidin-1-yl)prop-2-en-1-one;
1-(3-(4-amino-3-(4-(4-fluorophenoxy)-3-methylphenyl)-1H-pyrazolo[3,4-d]pyrimidin-1-yl)piperidin-1-yl)prop-2-en-1-one;
(R)-1-(3-(4-amino-3-(4-(4-fluorophenoxy)-3-methylphenyl)-1H-pyrazolo[3,4-d]pyrimidin-1-yl)piperidin-1-yl)prop-2-en-1-one;
(S)-1-(3-(4-amino-3-(4-(4-fluorophenoxy)-3-methylphenyl)-1H-pyrazolo[3,4-d]pyrimidin-1-yl)piperidin-1-yl)prop-2-en-1-one;
1-(3-(4-amino-3-(4-(3-(trifluoromethyl)phenoxy)phenyl)-1H-pyrazolo[3,4-d]pyrimidin-1-yl)piperidin-1-yl)prop-2-en-1-one;
(R)-1-(3-(4-amino-3-(4-(3-(trifluoromethyl)phenoxy)phenyl)-1H-pyrazolo[3,4-d]pyrimidin-1-yl)piperidin-1-yl)prop-2-en-1-one;
(S)-1-(3-(4-amino-3-(4-(3-(trifluoromethyl)phenoxy)phenyl)-1H-pyrazolo[3,4-d]pyrimidin-1-yl)piperidin-1-yl)prop-2-en-1-one;
(E)-1-(3-(4-amino-3-(3-fluoro-4-phenoxyphenyl)-1H-pyrazolo[3,4-d]pyrimidin-1-yl)piperidin-1-yl)-4-(dimethylamino)but-2-en-1-one;
(R,E)-1-(3-(4-amino-3-(3-fluoro-4-phenoxyphenyl)-1H-pyrazolo[3,4-d]pyrimidin-1-yl)piperidin-1-yl)-4-(dimethylamino)but-2-en-1-one;
(S,E)-1-(3-(4-amino-3-(3-fluoro-4-phenoxyphenyl)-1H-pyrazolo[3,4-d]pyrimidin-1-yl)piperidin-1-yl)-4-(dimethylamino)but-2-en-1-one;
(E)-1-(3-(4-amino-3-(3-chloro-4-phenoxyphenyl)-1H-pyrazolo[3,4-d]pyrimidin-1-yl)piperidin-1-yl)-4-(dimethylamino)but-2-en-1-one;
(R,E)-1-(3-(4-amino-3-(3-chloro-4-phenoxyphenyl)-1H-pyrazolo[3,4-d]pyrimidin-1-yl)piperidin-1-yl)-4-(dimethylamino)but-2-en-1-one;
(S,E)-1-(3-(4-amino-3-(3-chloro-4-phenoxyphenyl)-1H-pyrazolo[3,4-d]pyrimidin-1-yl)piperidin-1-yl)-4-(dimethylamino)but-2-en-1-one;
(E)-1-(3-(4-amino-3-(4-(4-chlorophenoxy)phenyl)-1H-pyrazolo[3,4-d]pyrimidin-1-yl)piperidin-1-yl)-4-(dimethylamino)but-2-en-1-one;

(R,E)-1-(3-(4-amino-3-(4-(4-chlorophenoxy)phenyl)-1H-pyrazolo[3,4-d]pyrimidin-1-yl)piperidin-1-yl)-4-(dimethylamino)but-2-en-1-one;

(S,E)-1-(3-(4-amino-3-(4-(4-chlorophenoxy)phenyl)-1H-pyrazolo[3,4-d]pyrimidin-1-yl)piperidin-1-yl)-4-(dimethylamino)but-2-en-1-one;

(E)-1-(3-(4-amino-3-(4-(4-fluorophenoxy)phenyl)-1H-pyrazolo[3,4-d]pyrimidin-1-yl)piperidin-1-yl)-4-(dimethylamino)but-2-en-1-one;

(R,E)-1-(3-(4-amino-3-(4-(4-fluorophenoxy)phenyl)-1H-pyrazolo[3,4-d]pyrimidin-1-yl)piperidin-1-yl)-4-(dimethylamino)but-2-en-1-one;

(S,E)-1-(3-(4-amino-3-(4-(4-fluorophenoxy)phenyl)-1H-pyrazolo[3,4-d]pyrimidin-1-yl)piperidin-1-yl)-4-(dimethylamino)but-2-en-1-one;

and the like, or a pharmaceutically acceptable salt, solvate, or a prodrug, or a metabolite thereof.

In some embodiments, there are provided pharmaceutical compositions comprising a compound of Formula I and a pharmaceutically acceptable carrier. In certain embodiments, the compositions are for the treatment of a disease regulated by a protein kinase. In certain embodiments, the compositions are for or the treatment of a hyper-proliferative disorder. In some embodiments, the pharmaceutical compositions further comprise an anti-neoplastic agent, an immunosuppressant, an immunostimulant, or combination thereof. In other embodiments, the pharmaceutical compositions are suitable for oral, parenteral, or intravenous administration In some embodiments, the present invention provides methods for regulating the kinase signaling transduction, said methods comprising administrating to a mammalian subject a therapeutically effective amount of a compound of Formula I.

In other embodiments, there are provided herein methods for treating or preventing a Bruton's tyrosine kinase (Btk) mediated disorder, said method comprising administrating to a mammalian subject a therapeutically effective amount of a compound of Formula I.

In yet another aspect, there are provided herein methods for inhibiting human epidermal growth factor receptor (HER) kinases, said methods comprising administrating to a mammalian subject a therapeutically effective amount of a compound of Formula I.

In other embodiments, there are provided herein methods for treating neoplasia, said methods comprising administrating to a mammalian subject in need of treatment, a therapeutically effective amount of a compound of Formula I. In certain embodiments, the neoplasia is selected from B cell malignancies, liver cancer, skin cancer, leukemia, colon carcinoma, renal cell carcinoma, gastrointestinal stromal cancer, solid tumor cancer, myeloma, breast cancer, pancreatic carcinoma, non-small cell lung cancer, non-Hodgkin's lymphoma, hepatocellular carcinoma, thyroid cancer, bladder cancer, colorectal cancer and prostate cancer. In certain embodiments, chronic lymphocytic leukemia, mantle cell lymphoma, diffuse large B-cell lymphoma, and multiple myeloma, breast cancer or the lung cancer.

Definitions

The term "alkyl" is intended to include straight, branched, and cyclic hydrocarbon groups, which contain only single carbon-carbon bonds and which may be unsubstituted or optionally substituted with one or more functional groups. Representative examples include methyl, ethyl, propyl, isopropyl, cyclopropyl, butyl, isobutyl, tert-butyl, cyclobutyl, pentyl, cyclopentyl, hexyl, and cyclohexyl, all of which may be optionally substituted. The preferred chain length of an alkyl group is from 1 to 6 carbon atoms. $C_1$-$C_6$ alkyl is intended to include $C_1$, $C_2$, $C_3$, $C_4$, $C_5$ and $C_6$ alkyl groups. Alkyl may be substituted or unsubstituted. Typical substituent groups include cycloalkyl, aryl, heteroaryl, heteroalicyclic, hydroxy, alkoxy, aryloxy, mercapto, alkylthio, arylthio, cyano, halo, carbonyl, thiocarbonyl, O-carbamyl, N-carbamyl, O-thiocarbamyl, N-thiocarbamyl, C-amido, N-amido, C-carboxy, O-carboxy, nitro, silyl, amino and —$NR^XR^Y$, wherein $R^X$ and $R^Y$ are independently selected from the group consisting of hydrogen, alkyl, cycloalkyl, aryl, carbonyl, acetyl, sulfonyl, trifluoromethanesulfonyl and, combined, a five- or six-member heteroalicyclic ring. Illustrative substituted alkyl group include, but are not limited to, fluoromethyl, difluoromethyl, trifluoromethyl, hydoxymethyl, methoxymethyl, 2-fluoroethyl, 2-methoxyethyl, etc.

The term "alkoxy" refers to both an —O-(alkyl) or an —O-(unsubstituted cycloalkyl) group. $C_1$-$C_6$ alkoxy is intended to include $C_1$-$C_6$ alkyl groups, wherein $C_1$-$C_6$ alkyl is defined above. Representative examples include, but are not limited to, methoxy, ethoxy, propoxy, butoxy, cyclopropyloxy, cyclobutyloxy, cyclopentyloxy, cyclohexyloxy, and the like.

The invention also includes isotopically-labeled compounds of the invention, wherein one or more atoms is replaced by an atom having the same atomic number, but an atomic mass or mass number different from the atomic mass or mass number usually found in nature. Examples of isotopes suitable for inclusion in the compounds of the invention include isotopes of hydrogen, such as deuterium and carbon such as $^{13}C$. Certain isotopically-labeled compounds of the invention, for example, those incorporating a radioactive isotope, are useful in drug and/or substrate tissue distribution studies. Substitution with heavier isotopes such as deuterium may afford certain therapeutic advantages resulting from greater metabolic stability, for example, increased in vivo half-life or reduced dosage requirements, and hence may be preferred in some circumstances. Isotopically-labeled compounds of the invention can generally be prepared by conventional techniques known to those skilled in the art or by processes analogous to those described herein, using an appropriate isotopically-labeled reagent in place of the non-labeled reagent otherwise employed.

The term "comprising" is meant to be open-ended, including the indicated component(s), but not excluding other elements.

The term "pharmaceutically acceptable" when used with reference to a compound of Formulas I is intended to refer to a form of the compound that is safe for administration to a subject. For example, a free base, a salt form, a solvate, a hydrate, a prodrug or derivative form of a compound of Formulas I-II, which has been approved for mammalian use, via oral ingestion or any other route of administration, by a governing authority or regulatory agency, such as the Food and Drug Administration (FDA) of the United States, is pharmaceutically acceptable.

Included in the compounds of Formulas I are the pharmaceutically acceptable salt forms of the free-base compounds. The term "pharmaceutically-acceptable salts" embraces salts, commonly used to form alkali metal salts and to form addition salts of free acids or free bases, which have been approved by a regulatory agency. Salts are formed from ionic associations, charge-charge interactions, covalent bonding, complexation, coordination, etc. The nature of the salt is not critical, provided that it is pharmaceutically acceptable.

In some embodiments, the compound(s) of Formulas I are used to treat a subject by administering the compound(s) as a pharmaceutical composition. To this end, the compound(s), in one embodiment, are combined with one or more pharmaceutically acceptable excipients, including carriers, diluents or adjuvants, to form a suitable composition, which is described in more detail herein.

The term "excipient", as used herein, denotes any pharmaceutically acceptable additive, carrier, adjuvant, or other suitable ingredient, other than the active pharmaceutical ingredient (API), which is typically included for formulation and/or administration purposes. "Diluent" and "adjuvant" are defined hereinafter.

The terms "treat", "treating," "treatment," and "therapy" as used herein refer to therapy, including without limitation, curative therapy, prophylactic therapy, and preventative therapy. Prophylactic treatment generally constitutes either preventing the onset of disorders altogether or delaying the onset of a pre-clinically evident stage of disorders in individuals.

The phrase "effective amount" is intended to quantify the amount of each agent, which will achieve the goal of improvement in disorder severity and the frequency of incidence over treatment of each agent by itself, while avoiding adverse side effects typically associated with alternative therapies. The effective amount, in one embodiment, is administered in a single dosage form or in multiple dosage forms.

The protection of functional groups by protecting groups, the protecting groups themselves, and their removal reactions (commonly referred to as "deprotection") are described, for example, in standard reference works, such as J. F. W. McOmie, *Protective Groups in Organic Chemistry*, Plenum Press, London and New York (1973), T. W. Greene and P. G. M. Wuts, *Protective Groups in Organic Synthesis*, Wiley, 3$^{rd}$ edition, John Wiley and Sons (1999), E. Gross and J. Meienhofer, *The Peptides*, Volume 3, Academic Press, London and New York (1981).

The invention further encompasses "intermediate" compounds, including structures produced from the synthetic procedures described, whether isolated or not, prior to obtaining the finally desired compound. Structures resulting from carrying out steps from a transient starting material, structures resulting from divergence from the described method(s) at any stage, and structures forming starting materials under the reaction conditions are all "intermediates" included in the invention. Further, structures produced by using starting materials in the form of a reactive derivative or salt, or produced by a compound obtainable by means of the process according to the invention and structures resulting from processing the compounds of the invention in situ are also within the scope of the invention.

Starting materials of the invention, are either known, commercially available, or can be synthesized in analogy to or according to methods that are known in the art. Many starting materials may be prepared according to known processes and, in particular, can be prepared using processes described in the examples. In synthesizing starting materials, functional groups in some cases are protected with suitable protecting groups when necessary. Protecting groups, their introduction and removal are described above.

The compounds of this invention in some embodiments also are represented in multiple tautomeric forms. The invention expressly includes all tautomeric forms of the compounds described herein.

The compounds in one embodiment also occur in cis- or trans- or E- or Z-double bond isomeric forms. All such isomeric forms of such compounds are expressly included in the present invention.

Indication

The present invention provides compounds which are capable of modulating one or more signal transduction pathways comprising, but not limited to Bruton's tyrosine kinase (Btk), or/and EGFR-T790M kinase. By the term "modulate," it is meant that the functional activity of the pathway (or a component thereof) is changed in comparison to its normal activity in the absence of the compound. This effect includes any quality or degree of modulation, including, increasing, agonizing, augmenting, enhancing, facilitating, stimulating, decreasing, blocking, inhibiting, reducing, diminishing, antagonizing, etc.

The compounds of the present invention may also modulate one or more of the following processes, including, but not limited to, e.g., cell growth (including, e.g., differentiation, cell survival, and/or proliferation), tumor cell growth (including, e.g., differentiation, cell survival, and/or proliferation), tumor regression, endothelial cell growth (including, e.g., differentiation, cell survival, and/or proliferation), angiogenesis (blood vessel growth), lymphangiogenesis (lymphatic vessel growth), and/or hematopoiesis (e.g., T- and B-cell development, dendritic cell development, etc.).

While not wishing to be bound by any theory or mechanism of action, it has been found that compounds of the present invention possess the ability to modulate kinase activity. The methods of the present invention, however, are not limited to any particular mechanism or how the compounds achieve their therapeutic effect. By the phrase "kinase activity," it is meant a catalytic activity in which a gamma-phosphate from adenosine triphosphate (ATP) is transferred to an amino acid residue (e.g., serine, threonine, or tyrosine) in a protein substrate. A compound can modulate kinase activity, e.g., inhibiting it by directly competing with ATP for the ATP-binding pocket of the kinase, by producing a conformational change in the enzyme's structure that affects its activity (e.g., by disrupting the biologically-active three-dimensional structure), by binding to and locking the kinase in an inactive conformation, etc.

Routes of Administration

Suitable routes of administration include, but are not limited to, oral, intravenous, rectal, aerosol, parenteral, ophthalmic, pulmonary, transmucosal, transdermal, vaginal, otic, nasal, and topical administration. In addition, by way of example only, parenteral delivery includes intramuscular, subcutaneous, intravenous, intramedullary injections, as well as intrathecal, direct intraventricular, intraperitoneal, intralymphatic, and intranasal injections.

The compounds of the invention may be administered orally. Oral administration may involve swallowing, so that the compound enters the gastrointestinal tract, or buccal or sublingual administration may be employed by which the compound enters the blood stream directly from the mouth. Formulations suitable for oral administration include solid formulations such as tablets, capsules containing particulates, liquids, or powders, lozenges (including liquid-filled), chews, multi- and nanoparticulates, gels, solid solution, liposome, films (including muco-adhesive), ovules, sprays and liquid formulations.

Liquid formulations include suspensions, solutions, syrups and elixirs. Such formulations may be used as fillers in soft or hard capsules and typically include a carrier, for example, water, ethanol, polyethylene glycol, propylene glycol, methylcellulose, or a suitable oil, and one or more emulsifying agents and/or suspending agents. Liquid formulations may also be prepared by the reconstitution of a solid, for example, from a sachet.

The compounds of the invention may also be used in fast-dissolving, fast-disintegrating dosage forms such as those described in Expert Opinion in Therapeutic Patents, 11 (6), 981-986 by Liang and Chen (2001), the disclosure of which is incorporated herein by reference in its entirety.

Combinations

While the compounds of the invention can be dosed or administered as the sole active pharmaceutical agent, they can also be used in combination with one or more compounds of the invention or in conjunction with other agents. When administered as a combination, the therapeutic agents can be formulated as separate compositions that are administered simultaneously or sequentially at different times, or the therapeutic agents can be given as a single composition.

In some embodiments, methods for treatment of androgen receptor-dependent or androgen receptor-mediated conditions or diseases, such as proliferative disorders, including cancer, comprises administration to a mammal a compound of Formulas I in combination with at least one additional agent selected, by way of example only, alemtuzumab, arsenic trioxide, asparaginase (pegylated or non-), bevacizumab, cetuximab, platinum-based compounds such as cisplatin, cladribine, daunorubicin/doxorubicin/idarubicin, irinotecan, fludarabine, 5-fluorouracil, gemtuzumab, methotrexate, taxol, temozolomide, thioguanine, or classes of drugs including hormones (an antiestrogen, an antiandrogen, or gonadotropin releasing hormone analogues, interferons such as alpha interferon, nitrogen mustards such as busulfan or melphalan or mechlorethamine, retinoids such as tretinoin, topoisomerase inhibitors such as irinotecan or topotecan, tyrosine kinase inhibitors such as gefinitinib or imatinib, or agents to treat signs or symptoms induced by such therapy including allopurinol, filgrastim, granisetron/ondansetron/palonosetron, dronabinol.

Specifically, the administration of compounds of the present invention in some embodiments are in conjunction with additional therapies known to those skilled in the art in the prevention or treatment of cancer. The foregoing description is merely illustrative of the invention and is not intended to limit the invention to the disclosed compounds, compositions and methods.

Synthesis of Compounds

The compounds of Formulas I is synthesized according to the procedures described in the following Schemes to those skilled in the art, wherein the substituents are as defined for Formulas I above, except where further noted. The synthetic methods described below are merely exemplary, and the compounds of the invention may also be synthesized by alternate routes as appreciated by persons of ordinary skill in the art. Compound 1 is commercial available, and Compound 2 is commercial available, literature known or are prepared readily by following similar literature known procedures. The palladium catalyzed cross coupling reaction of Compound 1 and Compound 2 led to the synthesis of Compound 3. The reaction between Compound 3 and Compound 4 via Mitsunobu reaction followed by the deprotection of Boc group afforded Compound 5. The acylation of Compound 5 by Compound 6 generated Compound 7 that described in Formula I (Scheme 1).

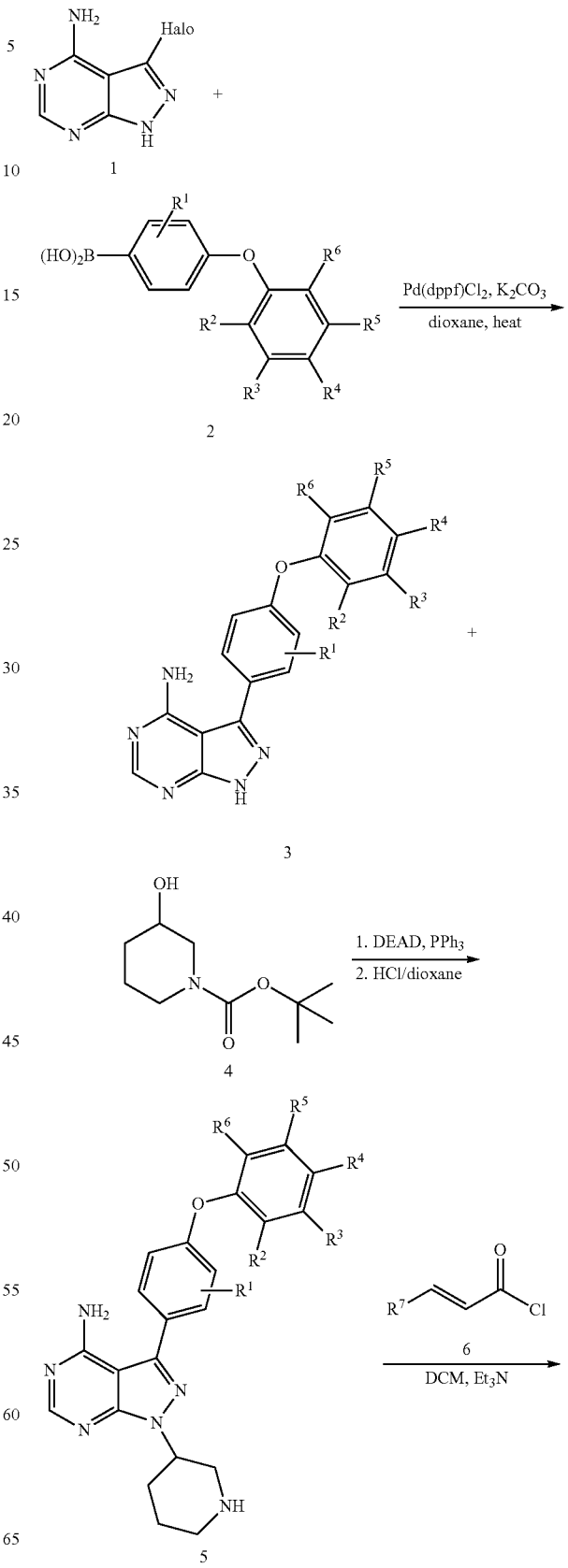

-continued

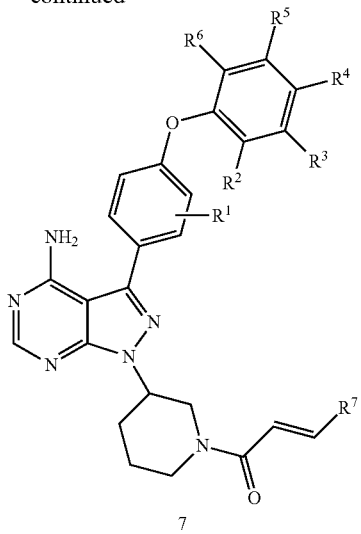
7

An alternative preparation of Compound 3 is described in Scheme 2. The palladium catalyzed cross coupling reaction between Compound 1 and boronate ester 8 afforded Compound 3.

pound 1A and Compound 9 afforded compound 10. The coupling reaction between Compound 10 and Compound 4 via Mitsunobu reaction afforded Compound 11. The deprotection of Boc group of compound 11 followed by acylation with acryloyl chloride afforded Compound 12.

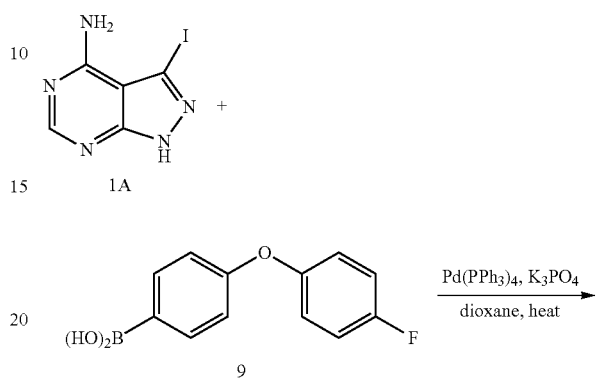

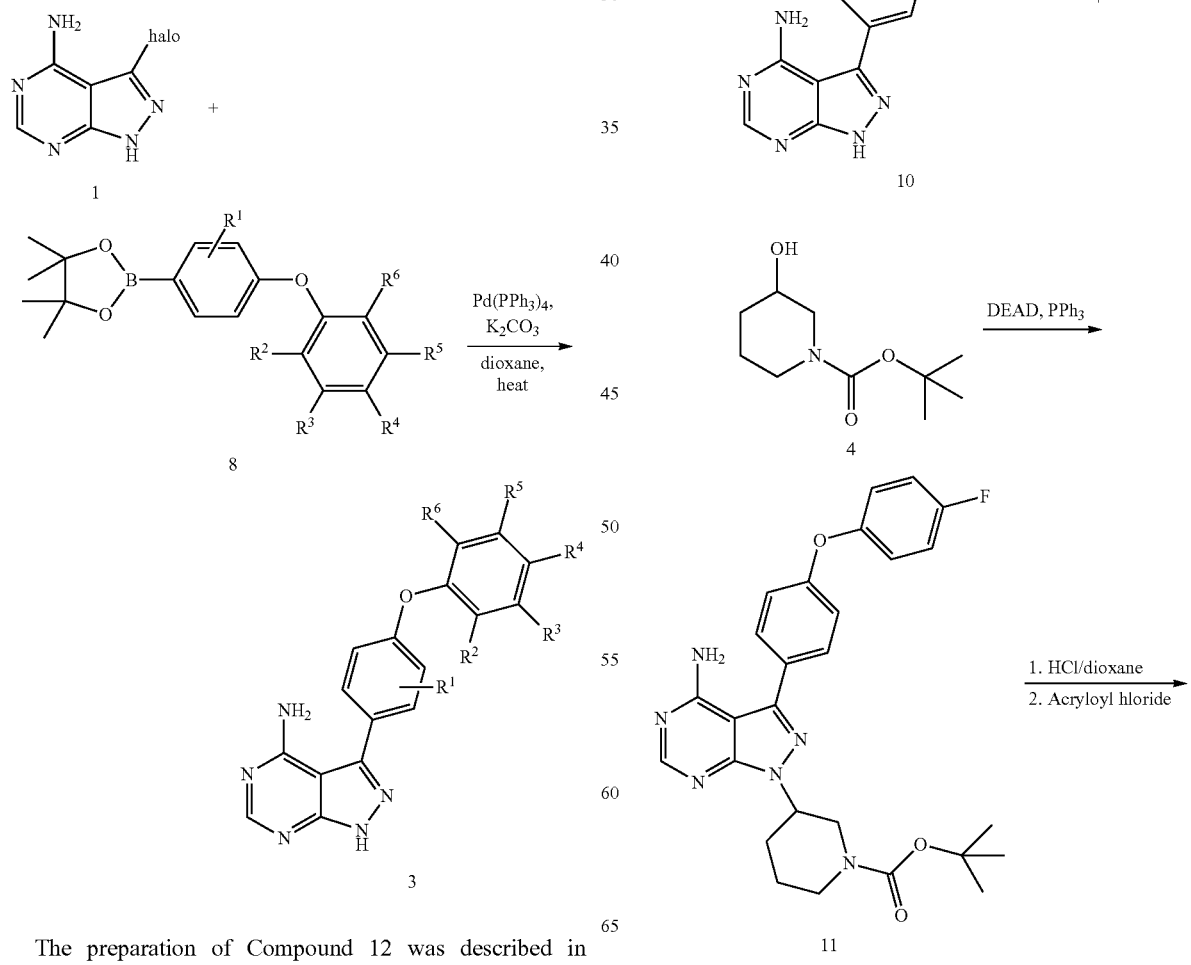

The preparation of Compound 12 was described in Scheme 3. The palladium catalyzed reaction between Com- -continued

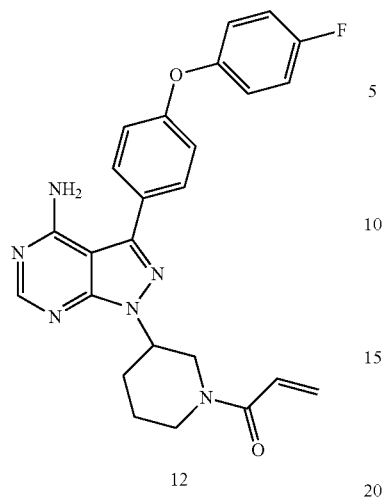

12

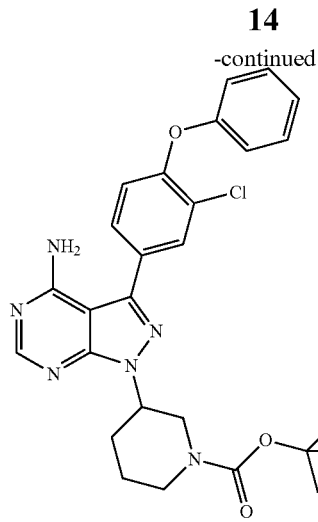

15

The synthesis of Compound 16 (Scheme 4) was following a similar procedure used to synthesize Compound 12 described in Scheme 3.

Scheme 4

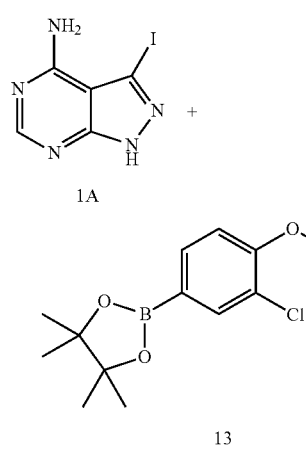

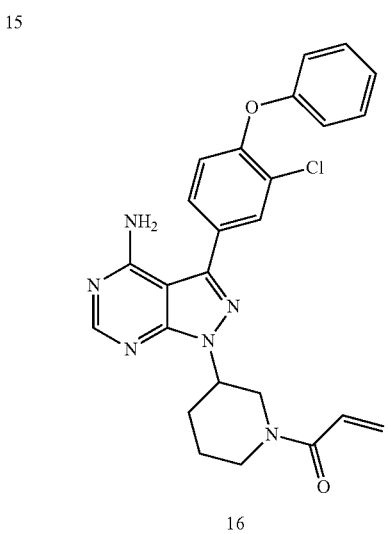

16

DESCRIPTION OF EMBODIMENTS

These detailed descriptions are presented for illustrative purposes only and are not intended as a restriction on the scope of the invention.

Proton NMR Spectra

Unless otherwise indicated, all $^1$H NMR spectra were run on a Varian series Mercury 300, 400 MHz instrument or a Bruker series 400 MHz instrument. Where so characterized, all observed protons are reported as parts-per-million (ppm) downfield from tetramethylsilane (TMS) or other internal reference in the appropriate solvent indicated.

Abbreviation

DMF means N,N-dimethylformamide.
DCM means dichloromethane.
Et$_3$N means triethylamine.
THF means tetrahydrofuran.
NIC means N-iodosuccinimide.
EA means ethyl acetate.
DEAD means diethyl azodicarboxylate.
RT means room temperature.

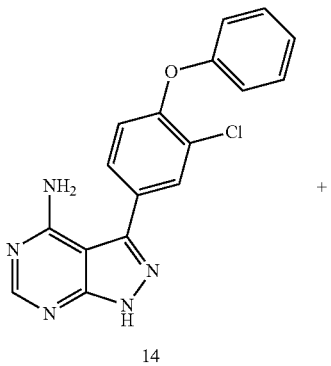

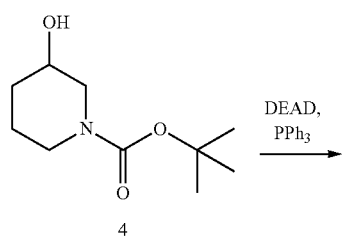

Example 1: The synthesis of (R)-1-(3-(4-amino-3-(4-(4-fluorophenoxy)phenyl)-1H-pyrazolo[3,4-d]pyrimidin-1-yl)piperidin-1-yl)prop-2-en-1-one (Compound 17)

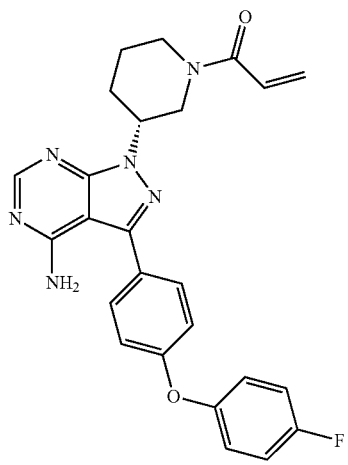 [SMILES: C=CC(=O)N1CCC[C@@H](n2nc(-c3ccc(Oc4ccc(F)cc4)cc3)c3c(N)ncnc32)C1]

1) A solution 1H-pyrazolo[3,4-d]pyrimidin-4-amine (5.0 g, 37 mmol, 1.00 eq) in DMF (50 mL) was cooled to 0° C. To the solution was added NIS (6.1 g, 38.9 mmol, 1.05 eq) portion wise. The reaction was heated at 60° C. for 24 hours, then saturated sodium bicarbonate solution was added. The reaction was stirred for another 30 minutes, filtered and concentrated to dryness under vacuum to give 3-iodo-1H-pyrazolo[3,4-d]pyrimidin-4-amine as a yellow solid 5.8 g.

2) To a solution of 4-(4,4,5,5-tetramethyl-1,3,2-dioxaborolan-2-yl)phenol (8.0 g, 36.3 mmol, 1.0 eq) in DCM (80 mL) was added 4-fluorophenylboronic acid (12.7 g, 90.7 mmol, 2.5 eq), Cu(OAc)$_2$ (10.5 g, 58.08 mmol, 1.6 eq) and Et$_3$N (22 g, 217.8 mmol, 6.0 eq). The resulting solution was stirred for overnight at RT. The solids were filtered, dried over anhydrous sodium sulfate, concentrated under vacuum, and purified by flash silica gel chromatograph with Ethyl acetate/Hexane (1:100) to give 2-(4-(4-fluorophenoxy)phenyl)-4,4,5,5-tetramethyl-1,3,2-dioxaborolane 6.3 g.

3) To a solution of 2-(4-(4-fluorophenoxy)phenyl)-4,4,5,5-tetramethyl-1,3,2-dioxaborolane (6.3 g, 20 mmol, 2.15 eq), 3-iodo-1H-pyrazolo[3,4-d]pyrimidin-4-amine (2.1 g, 9.3 mmol, 1.0 eq) and K$_2$CO$_3$ (4.5 g, 32.6 mmol, 3.5 eq) in DMF (20 mL) and water (10 mL), under a nitrogen was added Pd(dppf)Cl$_2$ 420 mg. The mixture was purged with bubbling nitrogen for 2 minutes, and then heated at 100° C. overnight. The reaction was cooled to room temperature, poured into water (100 mL), extracted with ethyl acetate (6×50 mL) and concentrated. The crude product was purified by flash chromatography on silica gel to give the 3-(4-(4-fluorophenoxy)phenyl)-1H-pyrazolo[3,4-d]pyrimidin-4-amine 1.1 g.

4) To a solution of triphenyl phosphine (4.2 g, 16 mmol, 5.0 eq) in THF (10 mL) at 0° C. was added DEAD (2.6 g, 13 mmol, 4.0 eq) and 3-(4-(4-fluorophenoxy)phenyl)-1H-pyrazolo[3,4-d]pyrimidin-4-amine (1.0 g, 3.2 mmol, 1.0 eq). After stirred for 30 min. the reaction was added (S)-tert-butyl 3-hydroxypiperidine-1-carboxylate (1.19 g, 5.92 mmol, 2.0 eq). The resulting bright orange solution was stirred at RT overnight. The solvent was removed, and the crude was purified by flash column chromatography on silica gel to give (R)-tert-butyl 3-(4-amino-3-(4-(4-fluorophenoxy)phenyl)-1H-pyrazolo[3,4-d]pyrimidin-1-yl)piperidine-1-carboxylate 100 mg as an oil.

5) To a solution of (R)-tert-butyl 3-(4-amino-3-(4-(4-fluorophenoxy)phenyl)-1H-pyrazolo[3,4-d]pyrimidin-1-yl)piperidine-1-carboxylate (100 mg) in dioxane (3 mL) was added saturated HCl in dioxane (6 mL). The reaction mixture was stirred at RT for 4 hours, and then was adjusted to pH at 10 by saturated bicarbonate sodium. The aqueous solution was extracted with ethyl acetate (3×50 mL) and the combined organic layers were washed with brine, dried (MgSO$_4$), filtered, and concentrated. The crude product was purified by flash column chromatography on silica gel to give (R)-3-(3-fluoro-4-phenoxyphenyl)-1-(piperidin-3-yl)-1H-pyrazolo[3,4-d]pyrimidin-4-amine 60 mg.

6) To a solution of (R)-3-(3-fluoro-4-phenoxyphenyl)-1-(piperidin-3-yl)-1H-pyrazolo[3,4-d]pyrimidin-4-amine (60 mg, 0.15 mmol, 1.0 eq) and Et$_3$N (45 mg, 0.5 mmol, 3.0 eq) in DCM (5 mL) was added acryloyl chloride (15 mg, 0.16 mmol, 1.1 eq) slowly with stirring. The reaction mixture was stirred at RT for 30 min, and then water (60 mL) was added. The aqueous solution was extracted with ethyl acetate (3×30 mL). The combined organic layers were washed with brine, dried over (MgSO$_4$), filtered, and concentrated. Purification by flash column chromatography on silica gel to give (R)-1-(3-(4-amino-3-(4-(4-fluorophenoxy)phenyl)-1H-pyrazolo[3,4-d]pyrimidin-1-yl)piperidin-1-yl)prop-2-en-1-one 30 mg. $^1$H-NMR (DMSO-d$_6$, 400 MHz): δ9.10 (s, 1H), 8.63 (s, 1H), 8.15 (s, 1H), 7.72-7.36 (m, 3H), 7.36-7.32 (m, 2H), 7.25 (s, 1H), 7.12-7.00 (m, 6H), 6.26-6.21 (m, 1H), 4.05 (s, 3H), 3.19 (m, 2H), 2.31 (s, 6H); LCMS: 469 [M+1];

Example 2: The Synthesis of (R)-1-(3-(4-amino-3-(3-chloro-4-phenoxyphenyl)-1H-pyrazolo[3,4-d]pyrimidin-1-yl)piperidin-1-yl)prop-2-en-1-one (Compound 18)

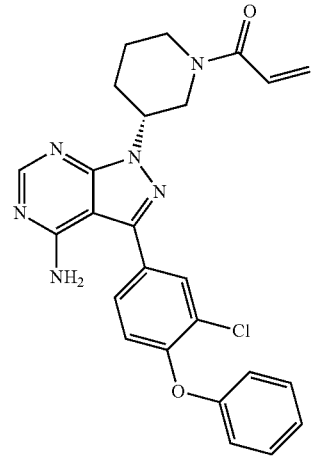 [SMILES: C=CC(=O)N1CCC[C@@H](n2nc(-c3ccc(Oc4ccccc4)c(Cl)c3)c3c(N)ncnc32)C1]

1) To a solution of 4-bromo-2-chlorophenol (30 g, 144.6 mmol, 1.0 eq) in DMF (250 mL) was added Bis(pinacolato)diboron (44 g, 173.5 mmol, 1.2 eq) and potassium acetate (49.6 g, 506.1 mmol, 3.5 eq). The reaction mixture was purged with nitrogen and dichlorobis(triphenylphosphino)palladium(II) (2 g, 2.85 mmol, 0.02 eq) was added. The reaction was heated at 80° C. for 24 hours, cooled to RT, filtered through celite and washed with ethyl acetate. The solid was dried over Na$_2$SO$_4$, filtered, and concentrated.

Purification by column chromatography on silica gel to give 2-chloro-4-(4,4,5,5-tetramethyl-1,3,2-dioxaborolan-2-yl)phenol 30 g as a yellow oil.

2) To a solution of 2-chloro-4-(4,4,5,5-tetramethyl-1,3,2-dioxaborolan-2-yl)phenol (20 g, 78.6 mmol, 1.0 eq) in DCM (160 mL), was added phenylboronic acid (24 g, 196.5 mmol, 2.5 eq), Cu(OAc)$_2$ (22.8 g, 125.7 mmol, 1.6 eq), Et$_3$N (47.6 g, 471.6 mmol, 6.0 eq). The resulting solution was stirred for overnight at RT. The solids were filtered, dried over anhydrous sodium sulfate and concentrated under vacuum. Purification by silica gel column with ethyl acetate/n-Hexane (1:100) afforded 2-(3-chloro-4-phenoxyphenyl)-4,4,5,5-tetramethyl-1,3,2-dioxaborolane 9 g.

3) To a solution of 2-(3-chloro-4-phenoxyphenyl)-4,4,5,5-tetramethyl-1,3,2-dioxaborolane (5.06 g, 15.3 mmol, 2.0 eq), 3-iodo-1H-pyrazolo[3,4-d]pyrimidin-4-amine (2 g, 7.66 mmol, 1.0 eq), and K$_2$CO$_3$ (3.7 g, 26.8 mmol, 3.5 eq) in DMF (30 mL) and water (15 mL) under nitrogen was added Pd(dppf)Cl$_2$ 300 mg. The reaction mixture was purged with bubbling nitrogen for 2 minutes, and then heated at 100° C. overnight. The reaction was cooled to room temperature, poured into water (100 mL), extracted with ethyl acetate (6×50 mL), and concentrated. The crude product was purified by flash column chromatography on silica gel to give 3-(3-chloro-4-phenoxyphenyl)-1H-pyrazolo[3,4-d]pyrimidin-4-amine 1.0 g.

4) To a solution of triphenyl phosphine (3.88 g, 14.8 mmol, 5 eq) in THF (10 mL) at ° C. was added DEAD (2.4 g, 11.84 mmol, 4 eq) and 3-(3-chloro-4-phenoxyphenyl)-1H-pyrazolo[3,4-d]pyrimidin-4-amine (1 g, 2.96 mmol, 1.0 eq). The reaction was stirred for 30 min before added (S)-tert-butyl 3-hydroxypiperidine-1-carboxylate (1.19 g, 5.92 mmol, 2.0 eq). The resulting bright orange solution was stirred at RT overnight, the solvent was removed and the crude product was purified by flash column chromatography on silica gel to give (R)-tert-butyl 3-(4-amino-3-(3-chloro-4-phenoxyphenyl)-1H-pyrazolo[3,4-d]pyrimidin-1-yl)piperidine-1-carboxylate 300 mg.

5) To a solution of (R)-tert-butyl 3-(4-amino-3-(3-chloro-4-phenoxyphenyl)-1H-pyrazolo[3,4-d]pyrimidin-1-yl)piperidine-1-carboxylate (300 mg) in dioxane (3 mL) was added saturated HCl in dioxane. The reaction mixture was stirred at RT for 4 hours, then the pH of the reaction mixture was adjusted to 10 by saturated bicarbonate sodium. The aqueous solution was extracted with ethyl acetate (3×50 mL), and the combined organic layers were washed with brine, dried (MgSO4), filtered, and concentrated. The crude product was purified by column chromatography on silica gel to give (R)-3-(3-chloro-4-phenoxyphenyl)-1-(piperidin-3-yl)-1H-pyrazolo[3,4-d]pyrimidin-4-amine 200 mg.

6) To a solution of (R)-3-(3-chloro-4-phenoxyphenyl)-1-(piperidin-3-yl)-1H-pyrazolo[3,4-d]pyrimidin-4-amine (200 mg, 0.48 mmol, 1.0 eq) and Et$_3$N (145 mg 1.44 mmol, 3.0 eq) in DCM (5 mL) was added acryloyl chloride (48 mg, 0.53 mmol, 1.1 eq) slowly. The reaction mixture was stirred at RT for 30 min, then water (60 ml) was added, The aqueous solution was extracted with ethyl acetate (3×30 mL), and the combined organic layers were washed with brine, dried (MgSO$_4$), filtered, and concentrated. Purification by flash column chromatography on silica gel to give (R)-1-(3-(4-amino-3-(3-chloro-4-phenoxyphenyl)-1H-pyrazolo[3,4-d]pyrimidin-1-yl)piperidin-1-yl)prop-2-en-1-one 100 mg. HNMR abd LCMS $^1$H-NMR (DMSO-d$_6$ 400 MHz): δ9.10 (s, 1H), 8.63 (s, 1H), 8.15 (s, 1H), 7.72-7.36 (m, 3H), 7.36-7.32 (m, 2H), 7.25 (s, 1H), 7.12-7.00 (m, 6H), 6.26-6.21 (m, 1H), 4.05 (s, 3H), 3.19 (m, 2H), 2.31 (s, 6H); LCMS: 469 [M−1];

Example 3: The synthesis of (R)-1-(3-(4-amino-3-(4-(3-fluorophenoxy)phenyl)-1H-pyrazolo[3,4-d]pyrimidin-1-yl)piperidin-1-yl)prop-2-en-1-one (Compound 19)

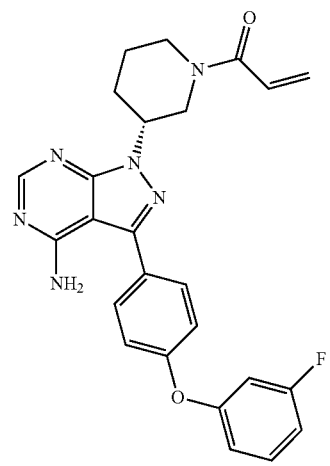 [SMILES: C=CC(=O)N1CCC[C@@H](n2nc(-c3ccc(Oc4cccc(F)c4)cc3)c3c(N)ncnc32)C1]

The title compound is synthesized according to the similar procedure described in Example 1. Staring material 3-fluorophenol is used. LCMS: 459 [M+1].

Example 4: The synthesis of (R)-1-(3-(4-amino-3-(3-fluoro-4-phenoxyphenyl)-1H-pyrazolo[3,4-d]pyrimidin-1-yl)piperidin-1-yl)prop-2-en-1-one (Compound 20)

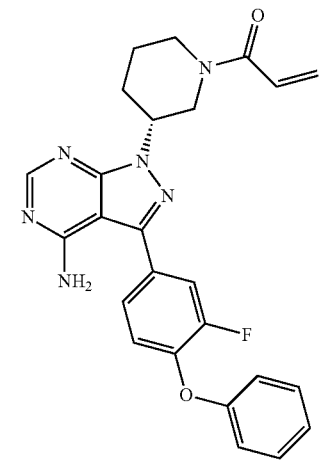 [SMILES: C=CC(=O)N1CCC[C@@H](n2nc(-c3ccc(Oc4ccccc4)c(F)c3)c3c(N)ncnc32)C1]

The title compound is synthesized according to the similar procedure described in Example 1. Staring material 2-(3- fluoro-4-phenoxyphenyl)-4,4,5,5-tetramethyl-1,3,2-dioxaborolane is used. LCMS: 459 [M+1].

Example 5: The synthesis of (R)-1-(3-(4-amino-3-(4-(4-chlorophenoxy)phenyl)-1H-pyrazolo[3,4-d]pyrimidin-1-yl)piperidin-1-yl)prop-2-en-1-one (Compound 21)

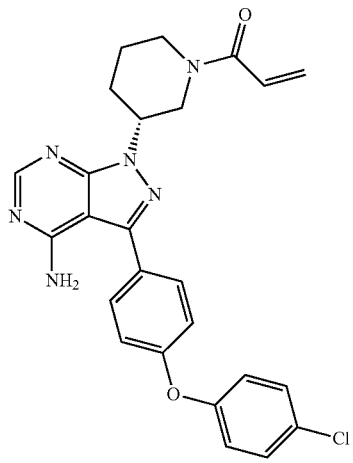 [SMILES: C=CC(=O)N1CCC[C@@H](n2nc(-c3ccc(Oc4ccc(Cl)cc4)cc3)c3c(N)ncnc32)C1]

The title compound is synthesized according to the similar procedure described in Example 1. Staring material 4-chlorophenol is used. LCMS: 475 [M+1].

Example 6: The synthesis of (R)-1-(3-(4-amino-3-(4-(4-chlorophenoxy)phenyl)-1H-pyrazolo[3,4-d]pyrimidin-1-yl)piperidin-1-yl)prop-2-en-1-one (Compound 22)

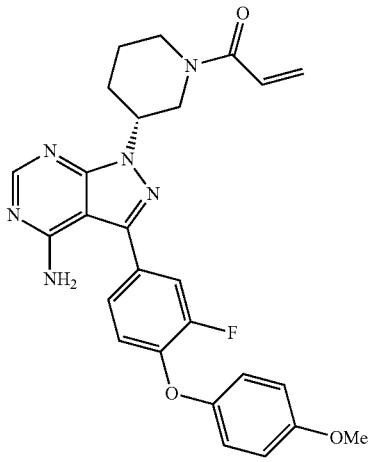 [SMILES: C=CC(=O)N1CCC[C@@H](n2nc(-c3ccc(Oc4ccc(OC)cc4)c(F)c3)c3c(N)ncnc32)C1]

The title compound is synthesized according to the similar procedure described in Example 1. Staring material 2-(3-fluoro-4-(4-methoxyphenoxy)phenyl)-4,4,5,5-tetramethyl-1,3,2-dioxaborolane is used. LCMS: 489 [M+1].

Biological Assays:

As stated herein before, the compounds defined in the present invention possess anti-proliferation activity. These properties may be assessed, for example, using one or more of the procedures set out below:

An in vitro assay which determines the ability of a test compound to inhibit EGFR (L858R), EGFR (L858R, T790M) and BTK kinases.

Kinase-tagged T7 phage strains were prepared in an *E. coli* host derived from the BL21 strain. *E. coli* were grown to log-phase and infected with T7 phage and incubated with shaking at 32° C. until lysis. The lysates were centrifuged and filtered to remove cell debris. The remaining kinases were produced in HEK-293 cells and subsequently tagged with DNA for qPCR detection. Streptavidin-coated magnetic beads were treated with biotinylated small molecule ligands for 30 minutes at room temperature to generate affinity resins for kinase assays. The liganded beads were blocked with excess biotin and washed with blocking buffer (SeaBlock (Pierce), 1% BSA, 0.05% Tween 20, 1 mM DTT) to remove unbound ligand and to reduce non-specific binding. Binding reactions were assembled by combining kinases, liganded affinity beads, and test compounds in 1× binding buffer (20% SeaBlock, 0.17×PBS, 0.05% Tween 20, 6 mM DTT). All reactions were performed in polystyrene 96-well plates in a final volume of 0.135 ml. The assay plates were incubated at room temperature with shaking for 1 hour and the affinity beads were washed with wash buffer (1×PBS, 0.05% Tween 20). The beads were then re-suspended in elution buffer (1x PBS, 0.05% Tween 20, 0.5 μM non-biotinylated affinity ligand) and incubated at room temperature with shaking for 30 minutes. The kinase concentration in the eluates was measured by qPCR.

An 11-point 3-fold serial dilution of each test compound was prepared in 100% DMSO at 100× final test concentration and subsequently diluted to 1× in the assay (final DMSO concentration=1%). Kds were determined using a compound top concentration=10,000 nM. If the initial Kd determined was <0.5 nM (the lowest concentration tested), the measurement was repeated with a serial dilution starting at a lower top concentration. A Kd value reported as 40,000 nM indicates that the Kd was determined to be >30,000 nM.

Binding constants (Kds) were calculated with a standard dose-response curve using the Hill equation: Response= Background+(Signal−Background)/(1+(Kd$^{Hill\ Slope}$/Dose$^{Hill\ Slope}$)). The Hill Slope was set to −1. Curves were fitted using a non-linear least square fit with the Levenberg-Marquardt algorithm.

The following Table 1 lists compounds representative of the invention and their corresponding inhibitory activity against EGFR(L858R), EGFR(L858R,T790M), and BTK.

TABLE 1

| No | EGFR (L858R) Kd (nM) | EGFR (L858R,T790M) Kd (nM) | BTK Kd (nM) |
| --- | --- | --- | --- |
| Compound 17 | 54 | 270 | <10 |
| Compound 18 | 6.3 | 9.3 | <10 |

A representative number of compounds were assayed against cancer cell line NCI-H1975 using the cell proliferation assay:

1. 5×10³ cells per well in 100 μl of medium were seeded in 96-well plate, here the medium contained 5% FBS
2. 24 hours later, 100 μl fresh medium was added with various concentrations of compounds into each well, while the medium here was free of FBS
3. After the cells were treated with compounds for 72 hours, 20 μl MTT (5 mg/ml) was added into each well, and then the assay plate was incubated at 37° C. for 4 more hours.

4. The assay plate was centrifuged at 800 g for 10 min. The medium was aspirated, 150 μl DMSO was added into each well. The plate was gently shaked for 10 min.

5. The absorbance at 570 nm was measured on the plate reader.

6. IR %=(WC−WT)/WC*100%.

The following Table 2 lists compound representative of the invention and its activity in NCI-H1975 cell proliferation assay.

TABLE 2

|  | Ibrutinib | Compound 18 |
| --- | --- | --- |
| NCI-H1975 | >2000 nM | 494 nM |

What is claimed is:

1. A compound according to Formula I:

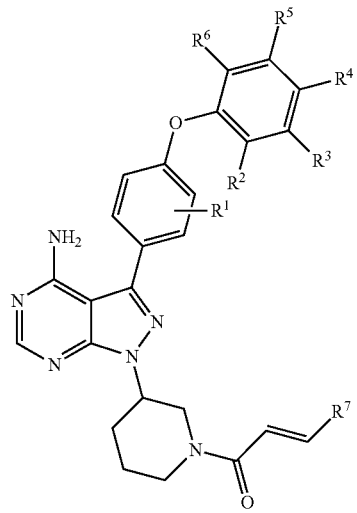

or a pharmaceutically acceptable salt, solvate or a stereoisomer or a tautomer thereof,
wherein $R^2$, $R^3$, $R^5$, $R^6$, and $R^7$ are hydrogen; $R^1$ and $R^4$ are independently hydrogen, F or Cl; and $R^1$ and $R^4$ are not both hydrogen.

2. A compound selected from the group consisting of:
1-(3-(4-amino-3-(3-fluoro-4-phenoxyphenyl)-1H-pyrazolo[3,4-d]pyrimidin-1-yl)piperidin-1-yl)prop-2-en-1-one;
(R)-1-(3-(4-amino-3-(3-fluoro-4-phenoxyphenyl)-1H-pyrazolo[3,4-d]pyrimidin-1-yl)piperidin-1-yl)prop-2-en-1-one;
(S)-1-(3-(4-amino-3-(3-fluoro-4-phenoxyphenyl)-1H-pyrazolo[3,4-d]pyrimidin-1-yl)piperidin-1-yl)prop-2-en-1-one;
1-(3-(4-amino-3-(3-chloro-4-phenoxyphenyl)-1H-pyrazolo[3,4-d]pyrimidin-1-yl)piperidin-1-yl)prop-2-en-1-one;
(R)-1-(3-(4-amino-3-(3-chloro-4-phenoxyphenyl)-1H-pyrazolo[3,4-d]pyrimidin-1-yl)piperidin-1-yl)prop-2-en-1-one;
(S)-1-(3-(4-amino-3-(3-chloro-4-phenoxyphenyl)-1H-pyrazolo[3,4-d]pyrimidin-1-yl)piperidin-1-yl)prop-2-en-1-one;
1-(3-(4-amino-3-(4-(4-chlorophenoxy)phenyl)-1H-pyrazolo[3,4-d]pyrimidin-1-yl)piperidin-1-yl)prop-2-en-1-one;
(R)-1-(3-(4-amino-3-(4-(4-chlorophenoxy)phenyl)-1H-pyrazolo[3,4-d]pyrimidin-1-yl)piperidin-1-yl)prop-2-en-1-one;
(S)-1-(3-(4-amino-3-(4-(4-chlorophenoxy)phenyl)-1H-pyrazolo[3,4-d]pyrimidin-1-yl)piperidin-1-yl)prop-2-en-1-one;
1-(3-(4-amino-3-(4-(4-fluorophenoxy)phenyl)-1H-pyrazolo[3,4-d]pyrimidin-1-yl)piperidin-1-yl)prop-2-en-1-one;
(R)-1-(3-(4-amino-3-(4-(4-fluorophenoxy)phenyl)-1H-pyrazolo[3,4-d]pyrimidin-1-yl)piperidin-1-yl)prop-2-en-1-one;
(S)-1-(3-(4-amino-3-(4-(4-fluorophenoxy)phenyl)-1H-pyrazolo[3,4-d]pyrimidin-1-yl)piperidin-1-yl)prop-2-en-1-one;
1-(3-(4-amino-3-(4-(3,4-dichlorophenoxy)phenyl)-1H-pyrazolo[3,4-d]pyrimidin-1-yl)piperidin-1-yl)prop-2-en-1-one;
(R)-1-(3-(4-amino-3-(4-(3,4-dichlorophenoxy)phenyl)-1H-pyrazolo[3,4-d]pyrimidin-1-yl)piperidin-1-yl)prop-2-en-1-one;
(S)-1-(3-(4-amino-3-(4-(3,4-dichlorophenoxy)phenyl)-1H-pyrazolo[3,4-d]pyrimidin-1-yl)piperidin-1-yl)prop-2-en-1-one;
1-(3-(4-amino-3-(4-(2-chloro-4-(trifluoromethyl)phenoxy)phenyl)-1H-pyrazolo[3,4-d]pyrimidin-1-yl)piperidin-1-yl)prop-2-en-1-one;
(R)-1-(3-(4-amino-3-(4-(2-chloro-4-(trifluoromethyl)phenoxy)phenyl)-1H-pyrazolo[3,4-d]pyrimidin-1-yl)piperidin-1-yl)prop-2-en-1-one;
(S)-1-(3-(4-amino-3-(4-(2-chloro-4-(trifluoromethyl)phenoxy)phenyl)-1H-pyrazolo[3,4-d]pyrimidin-1-yl)piperidin-1-yl)prop-2-en-1-one;
1-(3-(4-amino-3-(4-(4-fluorophenoxy)-3-methylphenyl)-1H-pyrazolo[3,4-d]pyrimidin-1-yl)piperidin-1-yl)prop-2-en-1-one;
(R)-1-(3-(4-amino-3-(4-(4-fluorophenoxy)-3-methylphenyl)-1H-pyrazolo[3,4-d]pyrimidin-1-yl)piperidin-1-yl)prop-2-en-1-one;
(S)-1-(3-(4-amino-3-(4-(4-fluorophenoxy)-3-methylphenyl)-1H-pyrazolo[3,4-d]pyrimidin-1-yl)piperidin-1-yl)prop-2-en-1-one;
1-(3-(4-amino-3-(4-(3-(trifluoromethyl)phenoxy)phenyl)-1H-pyrazolo[3,4-d]pyrimidin-1-yl)piperidin-1-yl)prop-2-en-1-one;
(R)-1-(3-(4-amino-3-(4-(3-(trifluoromethyl)phenoxy)phenyl)-1H-pyrazolo[3,4-d]pyrimidin-1-yl)piperidin-1-yl)prop-2-en-1-one;
(S)-1-(3-(4-amino-3-(4-(3-(trifluoromethyl)phenoxy)phenyl)-1H-pyrazolo[3,4-d]pyrimidin-1-yl)piperidin-1-yl)prop-2-en-1-one;
(E)-1-(3-(4-amino-3-(3-fluoro-4-phenoxyphenyl)-1H-pyrazolo[3,4-d]pyrimidin-1-yl)piperidin-1-yl)-4-(dimethylamino)but-2-en-1-one;
(R,E)-1-(3-(4-amino-3-(3-fluoro-4-phenoxyphenyl)-1H-pyrazolo[3,4-d]pyrimidin-1-yl)piperidin-1-yl)-4-(dimethylamino)but-2-en-1-one;
(S,E)-1-(3-(4-amino-3-(3-fluoro-4-phenoxyphenyl)-1H-pyrazolo[3,4-d]pyrimidin-1-yl)piperidin-1-yl)-4-(dimethylamino)but-2-en-1-one;
(E)-1-(3-(4-amino-3-(3-chloro-4-phenoxyphenyl)-1H-pyrazolo[3,4-d]pyrimidin-1-yl)piperidin-1-yl)-4-(dimethylamino)but-2-en-1-one;

(R,E)-1-(3-(4-amino-3-(3-chloro-4-phenoxyphenyl)-1H-pyrazolo[3,4-d]pyrimidin-1-yl)piperidin-1-yl)-4-(dimethylamino)but-2-en-1-one;

(S,E)-1-(3-(4-amino-3-(3-chloro-4-phenoxyphenyl)-1H-pyrazolo[3,4-d]pyrimidin-1-yl)piperidin-1-yl)-4-(dimethylamino)but-2-en-1-one;

(E)-1-(3-(4-amino-3-(4-(4-chlorophenoxy)phenyl)-1H-pyrazolo[3,4-d]pyrimidin-1-yl)piperidin-1-yl)-4-(dimethylamino)but-2-en-1-one;

(R,E)-1-(3-(4-amino-3-(4-(4-chlorophenoxy)phenyl)-1H-pyrazolo[3,4-d]pyrimidin-1-yl)piperidin-1-yl)-4-(dimethylamino)but-2-en-1-one;

(S,E)-1-(3-(4-amino-3-(4-(4-chlorophenoxy)phenyl)-1H-pyrazolo[3,4-d]pyrimidin-1-yl)piperidin-1-yl)-4-(dimethylamino)but-2-en-1-one;

1-(3-(4-amino-3-(4-(3-fluorophenoxy)phenyl)-1H-pyrazolo[3,4-d]pyrimidin-1-yl)piperidin-1-yl)prop-2-en-1-one;

(R)-1-(3-(4-amino-3-(4-(3-fluorophenoxy)phenyl)-1H-pyrazolo[3,4-d]pyrimidin-1-yl)piperidin-1-yl)prop-2-en-1-one;

(S)-1-(3-(4-amino-3-(4-(3-fluorophenoxy)phenyl)-1H-pyrazolo[3,4-d]pyrimidin-1-yl)piperidin-1-yl)prop-2-en-1-one;

(E)-1-(3-(4-amino-3-(4-(4-fluorophenoxy)phenyl)-1H-pyrazolo[3,4-d]pyrimidin-1-yl)piperidin-1-yl)-4-(dimethylamino)but-2-en-1-one;

(R,E)-1-(3-(4-amino-3-(4-(4-fluorophenoxy)phenyl)-1H-pyrazolo[3,4-d]pyrimidin-1-yl)piperidin-1-yl)-4-(dimethylamino)but-2-en-1-one; and (S,E)-1-(3-(4-amino-3-(4-(4-fluorophenoxy)phenyl)-1H-pyrazolo[3,4-d]pyrimidin-1-yl)piperidin-1-yl)-4-(dimethylamino)but-2-en-1-one.

3. A pharmaceutical composition comprising a compound of claim 1 and a pharmaceutically acceptable carrier.

\* \* \* \* \*